(12) United States Patent
Jin et al.

(10) Patent No.: US 8,461,227 B2
(45) Date of Patent: *Jun. 11, 2013

(54) RADICAL POLYMERIZABLE MACROCYCLIC RESIN COMPOSITIONS WITH LOW POLYMERIZATION STRESS

(75) Inventors: Xiaoming Jin, Middletown, DE (US); Paul D. Hammesfahr, Lewes, DE (US)

(73) Assignee: DENTSPLY International Inc., York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/655,626

(22) Filed: Jan. 4, 2010

(65) Prior Publication Data

US 2010/0240914 A1 Sep. 23, 2010

Related U.S. Application Data

(63) Continuation of application No. 12/381,860, filed on Mar. 17, 2009, now abandoned, which is a continuation of application No. 12/079,987, filed on Mar. 31, 2008, now abandoned, which is a continuation of application No. 11/153,089, filed on Jun. 15, 2005, now abandoned.

(60) Provisional application No. 60/579,837, filed on Jun. 15, 2004.

(51) Int. Cl.
*A61K 6/08* (2006.01)
*A61K 6/083* (2006.01)
*A61L 24/06* (2006.01)

(52) U.S. Cl.
USPC ........... 523/115; 523/113; 523/116; 523/118; 106/35; 433/226; 433/228.1

(58) Field of Classification Search
USPC ..... 523/116, 118, 115, 113; 106/35; 433/226, 433/228.1
See application file for complete search history.

(56) References Cited

U.S. PATENT DOCUMENTS

| | | | |
|---|---|---|---|
| 4,131,729 A | 12/1978 | Schmitt et al. | |
| 4,323,348 A * | 4/1982 | Schmitz-Josten et al. | 523/116 |
| 4,323,696 A | 4/1982 | Schmitz-Josten et al. | |
| 4,379,695 A | 4/1983 | Orlowski et al. | |
| 4,407,984 A | 10/1983 | Ratcliffe et al. | |
| 4,459,193 A | 7/1984 | Ratcliffe et al. | |
| 4,644,053 A | 2/1987 | Brunelle et al. | |
| 4,722,947 A | 2/1988 | Thanawalla et al. | |
| 4,744,827 A | 5/1988 | Winkel et al. | |
| 5,047,261 A | 9/1991 | Moussa et al. | |
| 5,110,893 A * | 5/1992 | Fukuyama | 528/125 |
| 5,321,117 A * | 6/1994 | Brunelle | 528/272 |
| 5,444,104 A | 8/1995 | Waknine | |
| 5,609,675 A | 3/1997 | Noritake et al. | |
| 5,621,119 A | 4/1997 | Podszun et al. | |
| 5,760,142 A | 6/1998 | Klee | |
| 5,792,821 A * | 8/1998 | Bowen | 506/19 |
| 5,846,075 A | 12/1998 | Shu et al. | |
| 5,856,374 A | 1/1999 | Ono et al. | |
| 5,886,064 A | 3/1999 | Rheinberger et al. | |
| 5,944,527 A | 8/1999 | Hasel | |
| 5,962,703 A | 10/1999 | Moszner et al. | |
| 5,998,499 A | 12/1999 | Klee et al. | |
| 6,022,940 A | 2/2000 | Byerley et al. | |
| 6,031,015 A | 2/2000 | Ritter et al. | |
| 6,037,444 A * | 3/2000 | Rannard et al. | 528/423 |
| 6,043,361 A | 3/2000 | Evans et al. | |
| 6,057,460 A | 5/2000 | Moszner et al. | |
| 6,096,903 A | 8/2000 | Moszner et al. | |
| 6,121,344 A | 9/2000 | Angeletakis et al. | |
| 6,127,450 A | 10/2000 | Angeletakis et al. | |
| 6,147,136 A | 11/2000 | Bissinger | |
| 6,177,534 B1 | 1/2001 | Antonucci et al. | |
| 6,184,339 B1 | 2/2001 | Stansbury et al. | |
| 6,187,836 B1 | 2/2001 | Oxman et al. | |
| 6,204,302 B1 | 3/2001 | Rawls et al. | |
| 6,232,367 B1 | 5/2001 | Kobashigawa et al. | |
| 6,262,142 B1 * | 7/2001 | Wang et al. | 523/116 |
| 6,344,556 B1 * | 2/2002 | Evans et al. | 540/467 |
| 6,353,040 B1 | 3/2002 | Subelka et al. | |
| 6,353,061 B1 | 3/2002 | Klee et al. | |
| 6,376,026 B1 * | 4/2002 | Correll et al. | 427/512 |
| 6,380,347 B1 * | 4/2002 | Lau et al. | 528/219 |
| 6,384,106 B1 | 5/2002 | Angeletakis | |
| 6,391,940 B1 | 5/2002 | Blackwell et al. | |
| 6,395,803 B1 | 5/2002 | Angeletakis | |
| 6,399,037 B1 | 6/2002 | Pflug et al. | |
| 6,448,301 B1 | 9/2002 | Gaddam et al. | |
| 6,495,643 B1 | 12/2002 | Evans et al. | |
| 6,566,413 B1 | 5/2003 | Weinmann et al. | |
| 2002/0025993 A1 | 2/2002 | Klee et al. | |
| 2002/0068771 A1 | 6/2002 | Klee et al. | |
| 2002/0128347 A1 | 9/2002 | Blackwell et al. | |
| 2003/0060535 A1 | 3/2003 | Moszner et al. | |
| 2003/0125435 A1 | 7/2003 | Norling et al. | |
| 2004/0077882 A1 | 4/2004 | Moszner et al. | |
| 2004/0106741 A1 | 6/2004 | Kriesel et al. | |
| 2005/0154199 A1 | 7/2005 | Whiteford et al. | |
| 2006/0287459 A1 | 12/2006 | Jin et al. | |

FOREIGN PATENT DOCUMENTS

| | | |
|---|---|---|
| WO | 9702787 A1 | 1/1997 |
| WO | 9917677 A1 | 4/1999 |
| WO | 0003688 A1 | 1/2000 |
| WO | 0195862 A1 | 12/2001 |
| WO | 2006002086 A1 | 1/2006 |

* cited by examiner

*Primary Examiner* — Michael Pepitone
(74) *Attorney, Agent, or Firm* — Leana Levin; Douglas J. Hura; David A. Zdurne

(57) ABSTRACT

A composition of macrocyclic oligomer with at least one polymerizable group, (meth)acrylate, for example.

6 Claims, No Drawings

RADICAL POLYMERIZABLE MACROCYCLIC RESIN COMPOSITIONS WITH LOW POLYMERIZATION STRESS

RELATED APPLICATIONS

This is a non-provisional application which is a continuation of USSN 12/381,860 filed Mar. 17, 2009 (now abandoned), which is a continuation of USSN 12/079,987 filed Mar. 31, 2008 (now abandoned), which is a continuation of USSN 11/153,089 filed Jun. 15, 2005 (now abandoned), which claims priority from U.S. provisional patent application Ser. No. 60/579,837 (Case LDC-949B) filed on Jun. 15, 2004.

FIELD OF THE INVENTION

This invention relates to a composition that can primarily be used in dental composite to afford low curing shrinkage and low curing stress. More specifically, it includes a method to prepare new resin that features by its macrocyclic geometry. In addition it also includes a method to prepare another resin diluent that features by its bulky, cyclic, and mono polymerizable group. Of course, a resin composition containing the macrocyclic oligomer and the bulky diluent and a resin/filler composition thereafter, which feature by low shrinkage AND low stress, are included as well. The unique structural geometry of polymerizable macrocyclic oligomer determines its low shrink nature; and its unique structural combination with a bulky diluent enables low shrink accompany with low stress. The application of such a resin composition will not limit in dental composites or other application in restorative dentistry such as resin cement, bonding agent, liner, et al. It can be extended to any other field, in which low shrink and low stress is as critical as in restorative dentistry.

BACKGROUND OF THE INVENTION

Polymerization shrinkage of curable material is referred to the dimensional contraction during polymerization prior to the cured objective is developed. The covalent bond formation during polymerization bring monomer molecules closer than what they were in the normal van der Walls distance. This is the origin of polymerization shrinkage and it is also the origin of polymerization stress. Of course, the stress accumulation depends on how the materials are cured, that is, the polymerization kinetics.

The chemical structure of a curable resin determines almost every property aspects for any cured objectives in certain extend. Then it comes with the process or technology through which the curing proceeds. Formulation is a process primarily regarding as a balance between individual ingredient and acceptable property by adjusting the composition. A process that integrates all components together should be included in the formulation stage as well. Other emerging parameters involved during the polymerization process such as curing light intensity and curing time and curing mode, definitely would affect any property associated the polymerization like shrinkage, stress and mechanical property. In this invention, only composition formulation part is covered. More particularly it regards new resin development and composite formulation thereafter.

It is well known that with increasing molecular weight, the mobility of polymeric chain would be limited, the diffusion is becoming the rate control factor. In addition, such a limited mobility in a cross-linking system appear to come earlier in comparison with linear system, which means extra reaction would lead to an increasing polymerization stress. There are different ways to control the stress generation and development:

1. Limit polymerization rate;
   Introducing a special rate controller like stable radicals;
   Creating different polymerization zones from which the stress developed in a polymerized zone could be transferred to its adjacent unpolymerized zone and got relief like segmental polymerization technique;
   Employing different polymerization groups;
   Using macromonomer to limit its reactivity at the early stage;
2. Limit polymerization conversion;
3. Limit cross-link density;

To reduce polymerization shrinkage and stress in the dental restorative composite, all of above approaches are taking into account as regards of chemistry approach. Besides, there is significant advance in the aspects of filler since it is composed of 60-90% in the entire composite. Increasing filler loading would lead to increasing in mechanical strength and reduction in polymerization shrinkage. Furthermore, the nature of filler, such as chemical composition, particle size and size distribution, surface character, silanization degree et al, have also demonstrated a tremendous impact on the balance between mechanical strength and shrinkage.

There is increasing demand for low shrinkage dental composite, since it was suggested that the lower polymerization shrinkage, the lower curing stress, then the higher clinically success in tooth restoration. However, such a correlation is not always true, this recommendation should be cautions. It is known that such recommendations for dental materials and clinical application techniques are frequently based on laboratory tests. However, if the lab test were based different methods, the recommendation would not make any sense. More specifically at the time being there is no standard method to evaluate the shrinkage and stress for dental materials, it should not be surprised to question any recommendation for particular dental material or product. Low shrinkage does not necessary grantee you low stress and less failure if the clinical operation is not proper, that it still quite technique sensitive procedure, not every clinician do it right. Just as an example, a new low shrinkage resin builds the foundation to a low shrinkage composite, but that does not assure that a low shrinkage product because the formulation and other associated technology can make it happen. Otherwise, the low shrinkage resin only means a good paper or paten, That is all. Same logical could be applied to tooth restoration with low shrinkage or even zero shrinkage composite, which is the base for a successful restoration but does not guaranteed it because it need highly trained clinician make it happen.

Polymerization shrinkage measurement is critical during low shrink material development, because it is important for establishing a reliable correlation between shrinkage and stress. It also helps for a fair judgement on low shrinkage composite to either clinician as dental material researchers. Unfortunately, there is no standard method by which polymerization shrinkage for resin or composite can be examined. Mercury dilatometer and gas pycnometer is employed in this laboratory to evaluate the polymerization shrinkage of resin and composite.

There are two different approaches to limit polymerization shrinkage and stress: chemical approach and technology approach. For light curable dental composite for instance, the chemical approach include new curing groups, new structural frames, new photoinitiator, new reaction kinetics, new coupling agent for new interface interaction between resin and fillers, and new filler et al; and technology approach includes:

new curing light source, new curing energy, new curing mode, new technique to create a cavity, new technique to fill the cavity et al. All of these processes determine the shrinkage and stress and their development, which are believed to be associated directly to a failure restoration.

This invention involves a chemical approach to limit polymerization shrinkage and stress. More particularly it regards a new resin and its composition development. In this invention, therefore, a general method is presented to make a polymerizable single net, such as a polymerizable macrocyclic oligomer, from which a 3D network would be developed via less direct polymerization of (meth)acrylate. Now the whole picture is clear: to pre-build a polymerizable macrocyclic as single net outside the tooth cavity first, then assembly it into a network inside the filled cavity with limited reaction. As a result for this new approach, the total shrinkage would be reduced due to the limited reaction group. However, the necessary mechanical property would not be significantly impaired because the cyclic nature can make easy in cross-link density development. In addition, a new mono(meth)acrylate with bulky side group was combined with the macrocyclic resin to generate a resin system that afford better balance regarding mechanical strength, polymerization shrinkage ands contraction stress. Finally a proper glass filler composition is also presented which determine the mechanical strength and handling property as well.

Cyclic and Macrocyclic Oligomers vs. Polymerizable Macrocyclic Oligomers

Various macrocyclic oligomers are well investigated since the researchers at GE developed a new approach to prepare cyclic carbonate oligomers. For example, in U.S. Pat. No. 4,644,053, it was disclosed a method to synthesize single macrocyclic compounds. Then various macrocyclics oligomers, including carbonates, esters, amides, ethers, imides, sulfides, et al, have been prepared. However, high temperature ring-opening reaction has to be involved to convert these macrocyclics into high molecular weight polymers. None of them could be further polymerizable without ring-opening.

Many photopolymerizable resins have been developed from mono-, di- or multiple functional resins to dendrimer, but no macrocyclic oligomer with multipolymerizable groups has been reported: U.S. Pat. No. 5,047,261, disclosed a composition containing a five-member carbonate cyclic group for fast copolymerization with mathacrylate.

U.S. Pat. No. 5,962,703, disclosed functionalized bicyclic methacrylate with norboneyl or norbonadienl group. U.S. Pat. No. 5,792,821, disclosed polymerizable cyclidextrin (CD) derivatives, in which various methacrylate was attached on CD. More recently, U.S. Pat. No. 6,043,361, disclosed polymerizable cyclic allylic sulfides is used for low shrinkage materials. All of these cyclic-related new resins are limited to small cyclic sizes that are exclude in the scope of this invention.

The occurrence of cyclization reaction is favorite at high dilution condition. However, its efficiency limits its possible application in commercial development. Fortunately a pseudo-high-dilution technology was developed to solve this problem. This technique was adopted here to prepare a polymerizable macrocyclic oligomers. More specifically, a free-radically polymerizable macrocyclic oligomers are prepared under pseudo-high-dilution condition via a condensation reaction between a reactive and free radical polymerizable precursor and various coupling agents. With such a method, various macrocyclics could be formed via any linkage to afford carbonate, ester, siloxane, phosphonate, and et al derivatives. On the other hand, the condensation groups usually have to be activated to assure a mild reaction for cyclization with the coupling monomers in order to avoid any premature polymerization of the pre-attached methacrylate groups. Typical reaction scheme is illustrated as following:

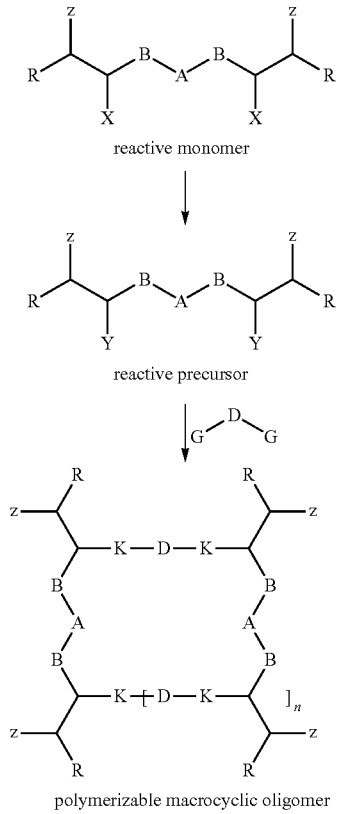

A: any aromatic or aliphatic or the combination moiety;

B: any linkage such as ether, thioether, ester, amide, carbonate, urethane, and urane, et al;

X: any reactive group such as hydroxyl, carboxyl, et al

Z: polymerizable groups like (meth)acrylate, vinyl, vinyl ether, and epoxy, et al R: any aromatic or aliphatic or the combination;

Y: any activated groups such as acylidied, acylamide, formated, carbonamade;

D: any of aromatic or aliphatic or their combination moiety;

The reactive monomer can be synthesized or commercially-available; It may not contain the primary polymerizable groups but the coupling agent must have at least one such a polymerizable group to ensure the formation of resulting ,macrocyclic oligomer to be further free-radical polymerizable.

SCHEME II

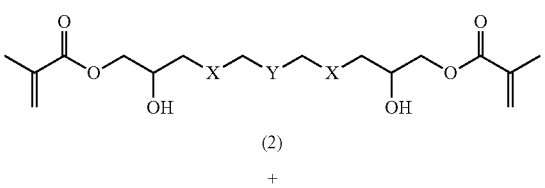

(2)

+

-continued

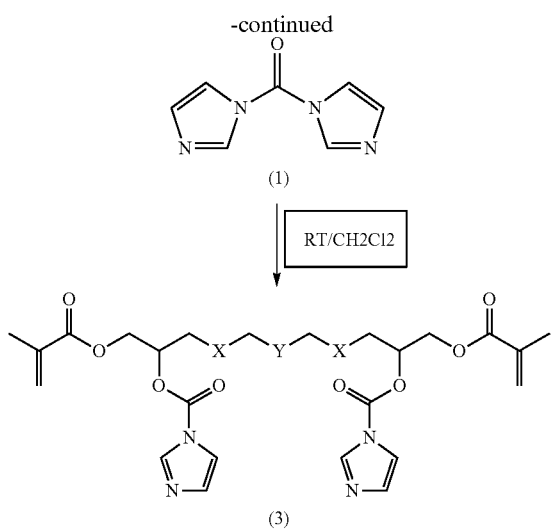

Y: Ar, cyclohexyl,
X: O, COO,

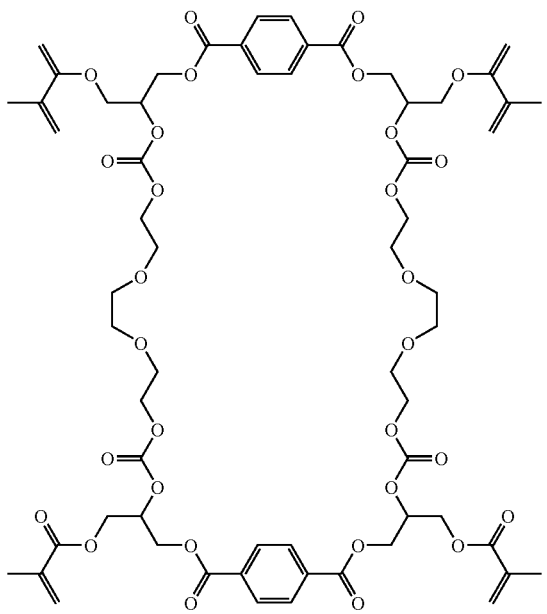 [SMILES: C=C(C)C(=C)OCC1COC(=O)c2ccc(cc2)C(=O)OCC(COC(=C)C(=C)C)OC(=O)OCCOCCOCCOC(=O)OC(COC(=O)C(=C)C)COC(=O)c2ccc(cc2)C(=O)OCC(COC(=O)C(=C)C)OC(=O)OCCOCCOCCOC(=O)O1]

BisGMA is one of widely used dental resin and it contains two free radical polymerizable group, methacrylate and two hydroxyl groups. This turns BisGMA an ideal candidate for polymerizable macrocyclic oligomer, although the presence of BisGMA isomer would make more complicated to this approach. As shown in Scheme II, carbonyldiimidazol (CDI, 1), was used to selectively reacted with the secondary alcohol in BisGMA (2) to give an activated BisGMA, DIZ-BisGMA (3). It was isolated and the chemical structure of DIZ-BisGMA was fully characterized with FITR and NMR. According to the recent report by Davis et al, CDI and its intermediates could exhibit surprisingly specificity towards primary, secondary, tertiary functional groups, of the same type, during the controlled formation of various well-defined molecular sequences [1-5]. In this invention, our idea is to adopt same chemistry of CDI and to selectively activate the two secondary hydroxyl groups in a free-radically polymerizable diol, BisGMA. Furthermore, the resulting precursor, DIZ-BisGMA, was made to react with various primary diols under a pseudo high-dilution condition, as shown in Scheme III, to generate macrocyclic carbonate oligomer bearing multiple polymerizable methacrylate groups. The two reactants were charged into the system in a high-dilution condition via two liquid pumps with slowly, precisely controlled addition in order to ensure a favorable formation of cyclic product. Actually cyclic product is accumulated within the reaction system and the final concentration can reach 0.02M, which is much higher than the classical high dilution condition (0.001M). However, the key to this procedure is to maintain a low initial concentration of reactants by controlled feeding. Therefore, it is referred as pseudo-high-dilution (PHD) method. The following examples will present the detailed procedure of the preparation of various precursors, macrocyclic oligomers, new cyclic diluent and composites thereafter.

EXAMPLE 1

34.4 g CDI was charged into a 1 liter, 3-neck round flask, which is equipped with a mechanic stirrer, condenser and nitrogen inlet. Then 200 ml of methylene chloride were added and slurry was formed. Once 140 ml solution of BisGMA in methylene chloride was introduced to the flask, the reaction system turned clear immediately. Allow the reaction run at room temperature for additional 4 hours before it was transfer to a volumetric flask. Be aware to add more solvent to bring up final volume of 500 ml, which is the necessary amount for next step macrocyclic reaction. It is not necessary to isolate the by-product from the precursor at this point because same compound will be generated during next cyclization process and it is not harmful to the cyclization as well. Sample can be taken from the final solution for FTIR analysis. Typical OH band should be totally disappeared and new carbonyl peak shifted to 1765 cm$^{-1}$ from 1718-1720 cm$^{-1}$ in BisGMA. If the precursor is isolated and purified, quantitative yield will be got.

EXAMPLE 2

Set up a 4 liter, 3-neck round flask, which is equipped with a mechanic stirrer, condenser and a two-arm liquid inlet. Connect the two liquid inlet arms to two separate liquid pumps, which will pump the two reactants, 500 ml each, into the reaction vessel at a controlled rate. The 500 ml of precursor prepared as above as one reactant, and another 500 ml solution of TetraEG (19.5 g) in methylene chloride as second reactant. Then add 40.0 g of potassium carbonate, 4.0 g of tetrabutyl ammonium bromide, 0.05 g of BHT, and 2000 ml of methylene chloride into the reaction vessel at room temperature. Then start to pump the two solutions into the reaction system at a rate of 80 ml per hour. All of the solution would be charged into the system in about 6-6.5 hrs. Then allow the reaction continue for additional 10-12 hrs before it was filtered to remove any solid. Part of the solvent can be stripped off and extracted the resulting solution with dilute acid, base and neutral water for several time to purify the product. Then the extracted solution was dried in magnium sulfate before removing all of the solvent. Clear, pale-yellow viscose resin is obtained. FTIR analysis confirmed the formation of cyclic carbonate by the carbonyl peak shifted back to 1740 cm-1 and less OH absorption at 3500-3800 cm-1, which suggest no or at least much less of the existence of hydroxyl end group. NMR and GPC analysis also support the formation of cyclic structure. It is mixture of macrocyclics with different size, and small amount of linear derivative is also evident. The overall yield of macrocyclic carbonate oligomer can be more than 95%.

EXAMPLE 3-15

Followed this general synthesis process as present in Example 2, instead of TetraEG, various diols were explored to prepare different macrocyclic carbonate oligomers.

EXAMPLE 16

As illustrated in example 1, new reactive dimethacylate, IPADMA was used instead of BisGMA to form different activated precursor; and accordingly, new macrocyclic carbonate was prepared.

EXAMPLE 17

As illustrated in Example 1, trichloride phosphonate was used in reaction with BisGMA to developing an activated phosphate, which then was used to form a macrocyclic phonate bearing polymerizable groups.

EXAMPLE 18

Dissolve 3.0 g DMAP and 98.2 g TCDCOH in 250 ml of THF and 250 ml of methylene chloride. Then add 90 ml TEA into this solution before it was transferred to a 1 liter, 3-neck round flask setting in an ice bath of 0-5 oC., which is equipped with a mechanic stirrer, condenser and a 200 ml addition funnel. Then 93.2 g of MAA in 100 ml of methylene chloride were added the addition funnel. Start to add the MAA solution dropwisely into the reaction system in a period of 2-3 hrs. Keep the reaction temperature around at 0-5° C. Allow the reaction to continue for additional 3-4 hrs after all of MAA solution was charged into the system. Extracted the resulting reaction solution with dilute acid, base and neutral solution, it was dried and further stripped to result a clear, colorless liquid. This is a mixture of dimethacrylate and monomethacrylate. The radio for TCDCDMA and TCDCMA is 1:5 to 1:2, more preferably is 1:3. FTIR analysis can verify the actual ratio. New carbonyl peak shifted to 1765 $cm^{-1}$ from 1778-1810 $cm^{-1}$ in MAA. Quantitative yield is for this TCDCMA/TCDCDMA mixture.

EXAMPLE 19

As illustrated in Example 2, an improved process was developed by add TCDCMA/TCDCDMA mixture into the resulting macrocyclic oligomer solution prior to final strip mixture. The weight ratio for this cyclic resin and the diluent resin should keep in about 2:1. This would make easy for the solvent removal and increase resin stability. The viscosity for this resin mixture can be 150-200 Pa·s at 25° C.

EXAMPLE 20

As illustrated in Example 19, the resulting resin mixture will formulate with additional 10-15% (wt/wt) of TCDCA (Aldrich) to result in proper resin mixture for low shrink composite. Its viscosity range from 50-75 Ps·s at 25° C.

EXAMPLE 21

CQ, EDAB, BHT and other necessary additives were admixed with the above resin mixture accordingly.

EXAMPLE 22

Glass filler mixtures with three different size distribution were premixed in as ration 60/20/20 or more preferably 55/30/15 (medium/coarse/fine particle).

EXAMPLE 23

Composite paste was made from 18-20% of the above-mentioned resin mixture and 80-82% BAFG filler mix. Its polymerization shrinkage ranged from 1.10-30% by dilatometer to 0.80-1.20% by gas pycnometer. This paste is condensable and demonstrated excellent packability with packability index of 1000 g/mm2. It can be easily extruded from a 2.1 mm compule with a typical extrusion force of 10 kgf. It has moderate overall mechanical strength such as compressive strength of 300 Mpa, compressive modulus of 7400 Mpa, flexural strength of 110-120 Mpa and flexural modulus is 9900-10000 Mpa. The 400K cycle local wear index is 0.05. The most important feature id its low curing strain of 750-850 ue, which is about ½ of TPH (1647) or SureFil (1865) composite.

COMPARISON EXAMPLE 1

Similar composite paste made from 18-20% of the conventional NCO monomers and 80-81% BAFG filler mix as presented by SureFil. It has polymerization shrinkage 2.30-2.20% by dilatometer or 2.50% by gas pycnometer, which are more 100% higher than the current experimental composite. SureFil possesses a packability index of 800 g/mm2. It also has superior mechanical property such as compressive strength of 340 Mpa, flexural strength of 140 Mpa and flexural modulus of 1200 Mpa. The 400K cycle local wear index is as low as 0.02. However, its curing strain reached 1865 ue, which is 130% higher than the experimental composite. This means the polymerization stress would be doubled in SureFil.

COMPARISON EXAMPLE 2

Another composite paste made from 22-23% of the conventional NCO monomers and 77-78% BABG filler mix as presented by TPH Spectrum. It has polymerization shrinkage 2.60-2.80% by dilatometer or 2.90% by gas pycnometer, which are more 100% higher than the current experimental composite. TPH Spectrum is not a packable materials, even it has excellent mechanical strength such as compressive strength of 380 Mpa, flexural strength of 130 Mpa and flexural modulus of 1100 Mpa. The 400K cycle local wear index is 0.06. Curing strain is 1650 ue, which is 110% higher than the experimental composite.

COMPARISON EXAMPLE 3

Another composite paste based on 21-22% of the different conventional resin mixture and more than 78% of BABG filler mix containing small amount nano-filler as presented by Experimental composite II. It has polymerization shrinkage 1.60% by dilatometer or 2.10% by gas pycnometer, which at least is 50% higher than the current experimental composite. This is a less packable materials, its packability index is only 650. But it does demonstrated good overall mechanical strength such as compressive strength of 320 Mpa, flexural strength of 110 Mpa and flexural modulus of 9000 Mpa. However, its curing strain is 1120 ue, which is 40% higher than the current experimental composite.

What is claimed is:

1. A dental composition comprising a macrocyclic oligomer with at least one (meth)acrylate polymerizable group, wherein the dental composition has a polymerization shrinkage from 1.10% to 30% as measured by a dilatometer,
wherein the macrocyclic oligomer is derived by condensing DIZ-BisGMA and primary diol.

2. A method of preparing a dental composition comprising a polymerizable macrocyclic oligomer, comprising the step of preparing the polymerizable macrocyclic oligomer by condensing DIZ-BisGMA and a primary diol at pseudo high-dilution conditions, wherein the dental composition has a polymerization shrinkage from 1.10% to 30% as measured by a dilatometer.

3. A method of preparing a dental composition comprising a polymerizable macrocyclic oligomer, comprising the step of condensing DIZ-BisGMA and a primary diol resulting in formation of the polymerizable macrocyclic oligomer, and combining the polymerizable macrocyclic oligomer with a mixture of dimethacrylate and monomethacrylate to form the dental composition, wherein the dental composition has a polymerization shrinkage from 1.10% to 30% as measured by a dilatometer.

4. The dental composition as in claim 1, wherein the dental composition has a curing strain of from 750 ue to 850 ue.

5. The method as in claim 2, wherein the dental composition has a curing strain of from 750 ue to 850 ue.

6. The method as in claim 3, wherein the dental composition has a curing strain of from 750 ue to 850 ue.

* * * * *